(12) United States Patent
Kato et al.

(10) Patent No.: US 8,128,567 B2
(45) Date of Patent: Mar. 6, 2012

(54) ULTRASONIC IMAGING APPARATUS

(75) Inventors: Sei Kato, Tokyo (JP); Takanori Saito, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 614 days.

(21) Appl. No.: 12/342,185

(22) Filed: Dec. 23, 2008

(65) Prior Publication Data

US 2009/0171215 A1  Jul. 2, 2009

(30) Foreign Application Priority Data

Dec. 26, 2007 (JP) .................. 2007-334438

(51) Int. Cl.
A61B 8/14 (2006.01)
A61B 8/00 (2006.01)
(52) U.S. Cl. ...................... 600/458; 600/437
(58) Field of Classification Search .............. 600/437, 600/458
See application file for complete search history.

(56) References Cited

U.S. PATENT DOCUMENTS

| | | | |
|---|---|---|---|
| 5,295,485 A | 3/1994 | Shinomura et al. | |
| 5,640,960 A | 6/1997 | Jones et al. | |
| 5,722,412 A | 3/1998 | Pflugrath et al. | |
| 5,763,785 A | 6/1998 | Chiang | |
| 5,817,024 A | 10/1998 | Ogle et al. | |
| 5,839,422 A | 11/1998 | Ferris | |
| 5,865,733 A | 2/1999 | Malinouskas et al. | |
| 5,970,025 A | 10/1999 | Cole et al. | |
| 6,007,499 A | 12/1999 | Martin et al. | |
| 6,102,863 A | 8/2000 | Pflugrath et al. | |
| 6,413,216 B1 | 7/2002 | Cain et al. | |
| 6,432,067 B1 | 8/2002 | Martin et al. | |
| 6,719,449 B1 | 4/2004 | Laugharn, Jr. et al. | |
| 7,239,907 B2 | 7/2007 | Abe et al. | |
| 7,258,674 B2 | 8/2007 | Cribbs et al. | |
| 2002/0138007 A1 | 9/2002 | Nguyen-Dinh et al. | |
| 2005/0131302 A1 | 6/2005 | Poland | |
| 2006/0030779 A1* | 2/2006 | Chomas et al. ............... 600/458 |

OTHER PUBLICATIONS

Revised Medical Ultrasonic Equipment Handbook, edited by Electronic Industries Association of Japan, Corona Publishing Co., Ltd., Jan. 20, 1997.

* cited by examiner

*Primary Examiner* — Michael Rozanski
(74) *Attorney, Agent, or Firm* — Armstrong Teasdale LLP (57) ABSTRACT

An ultrasonic imaging apparatus includes an image obtaining unit for irradiating an imaging region and obtaining tomographic image information that draws the imaging region, an input unit for inputting scan parameter value information and a target sound pressure parameter value as an index of an estimated sound pressure in the subject, an estimated maximum sound pressure parameter value calculating device for calculating an estimated maximum sound pressure parameter value in the subject on the basis of the scan parameter value information and maximum drive voltage information of a piezoelectric transducer group for generating an ultrasonic wave, and a maximum drive voltage optimization device for comparing the estimated maximum sound pressure parameter value and the target sound pressure parameter value and optimizing the maximum drive voltage value of the maximum drive voltage information.

16 Claims, 9 Drawing Sheets

ULTRASONIC IMAGING APPARATUS

CROSS REFERENCE TO RELATED APPLICATIONS

This application claims the benefit of Japanese Patent Application No. 2007-334438 filed Dec. 26, 2007, which is hereby incorporated by reference in its entirety.

BACKGROUND OF THE INVENTION

The embodiments described herein relate to an ultrasonic imaging apparatus for obtaining an image of a subject to which a contrast agent is injected.

In recent years, an image of a contrast agent injected to a subject is obtained by using an ultrasonic imaging apparatus. Ultrasound examinations using a contrast agent includes an examination of destroying the contrast agent and observing ultrasonic waves generated at the time of destruction and an examination of, without destroying the contrast agent, repeatedly irradiating the contrast agent with ultrasonic waves and observing a harmonic content in reflected ultrasonic waves from the contrast agent.

The contrast agent is destroyed by being irradiated with an ultrasonic wave of high sound pressure. Therefore, at the time of repetitively irradiating the contrast agent with ultrasonic waves and observing reflected ultrasound, the sound pressure of the ultrasonic wave to be applied has to be suppressed to a destruction sound pressure or less.

The ultrasonic sound pressure in the subject is expressed by using an MI (mechanical index) as an index of an action on a living body by ultrasonic cavitation. The MI value shows an amount proportional to the negative sound pressure in the ultrasonic wave in the subject and reflects the sound pressure in the subject (refer to, for example, "Revised medical ultrasonic equipment handbook" edited by Electronic Industries Association of Japan, Corona Publishing Co., Ltd., January 20, 1997, pp. 52 to 58). An estimated maximum MI value in a subject calculated by using scan parameter values or the like at the time of performing imaging is displayed on a display screen. The operator adjusts the magnitude of a maximum drive voltage at the time of driving piezoelectric transducers so that the estimated maximum MI value does not exceed a value at which the contrast agent is destroyed.

However, in the background art, each time the scan parameter value used for imaging is changed, the magnitude of the maximum drive voltage has to be re-adjusted. Specifically, in the case of changing the scan parameter values such as the electronic focus position and the aperture width, the maximum sound pressure generated in the subject changes, so that the estimated maximum MI value of a display screen to be calculated also changes.

Therefore, in the case of changing the scan parameter values, the operator has to simultaneously re-adjust the maximum drive voltage so as to maintain the estimated maximum MI value constant. It is a factor of deteriorating the operability in an examination using a contrast agent.

Consequently, it is important to realize an ultrasonic imaging apparatus in which the estimated maximum MI value in a subject is maintained at a predetermined value also in the case of changing the scan parameter values.

It is desirable that the problem described previously is solved.

BRIEF DESCRIPTION OF THE INVENTION

An ultrasonic imaging apparatus according to of a first aspect includes: an image obtaining unit for irradiating an imaging region in a subject to which a contrast agent is injected with an ultrasonic wave and obtaining tomographic image information that draws the imaging region; an input unit for inputting scan parameter value information which is set in the image obtaining unit and a target sound pressure parameter value of a sound pressure parameter as an index of an estimated sound pressure in the subject; an estimated maximum sound pressure parameter value calculating device, at the time of performing the irradiation, for calculating an estimated maximum sound pressure parameter value in the subject on the basis of the scan parameter value information and maximum drive voltage information of a piezoelectric transducer group for generating the ultrasonic wave; and a maximum drive voltage optimization device, each time the scan parameter value information is changed, for comparing the estimated maximum sound pressure parameter value calculated by using the estimated maximum sound pressure parameter value calculating device and the target sound pressure parameter value with each other and optimizing the maximum drive voltage value of the maximum drive voltage information.

In the first aspect, each time the scan parameter value information is changed, the estimated maximum sound pressure parameter value and the target sound pressure parameter value are compared with each other, and the maximum drive voltage information is optimized by the maximum drive voltage optimization device.

An ultrasonic imaging apparatus according to a second aspect includes: an image obtaining unit for irradiating an imaging region in a subject to which a contrast agent is injected with an ultrasonic wave and obtaining tomographic image information that draws the imaging region; an input unit for inputting scan parameter value information which is set in the image obtaining unit and a target MI value in the subject; an estimated maximum MI value calculating device, at the time of performing the irradiation, for calculating an estimated maximum MI value in the subject on the basis of the scan parameter value information and maximum drive voltage information of a piezoelectric transducer group for generating the ultrasonic wave; and a maximum drive voltage optimization device, each time the scan parameter value information is changed, for comparing the estimated maximum MI value calculated by using the estimated maximum MI value calculating device and the target MI value with each other and optimizing the maximum drive voltage value of the maximum drive voltage information.

In the second aspect, each time the scan parameter value information is changed, the estimated maximum MI value and the target MI value are compared with each other, and the maximum drive voltage information is optimized by the maximum drive voltage optimization device.

In a third aspect, in the ultrasonic imaging apparatus according to the second aspect, the maximum drive voltage optimization device changes the maximum drive voltage value to perform optimization so that the estimated maximum MI value becomes equal to or less than the target MI value.

In the third aspect, in the case where the target MI value is the upper limit value of the MI value at which the contrast agent is not destroyed, the maximum drive voltage is set to a voltage at which the contrast agent is not destroyed.

In a fourth aspect, in the ultrasonic imaging apparatus according to the third aspect, the maximum drive voltage optimization device has a voltage value monotonous decreasing device for gradually decreasing a drive voltage value of the piezoelectric transducer group from an overvoltage value at which the estimated maximum MI value exceeds the target MI value at predetermined voltage intervals.

In the fourth aspect, the optimum value is searched in order from the largest maximum drive voltage value by the voltage value monotonous decreasing device.

In a fifth aspect, in the ultrasonic imaging apparatus according to the fourth aspect, the input unit has a voltage interval setting device for setting the voltage interval.

In the fifth aspect, precision for optimization and search time is adjusted.

In a sixth aspect, in the ultrasonic imaging apparatus according to the fourth or fifth aspect, the maximum drive voltage optimization device sets an initial maximum drive voltage value at which the estimated maximum MI value becomes equal to or less than the target MI value to an optimized maximum drive voltage value.

In the sixth aspect, the estimated maximum MI value is set as the highest value equal to or less than the target MI value, and high-sensitivity tomographic image information is obtained.

In a seventh aspect, in the ultrasonic imaging apparatus according to the third aspect, the maximum drive voltage optimization device has, as the maximum drive voltage information, a first maximum drive voltage value at which the estimated maximum MI value exceeds the target MI value and a second maximum drive voltage value smaller than the first maximum drive voltage value.

In the seventh aspect, as variables of optimization, the first and second maximum drive voltage values are used.

In an eighth aspect, in the ultrasonic imaging apparatus according to the seventh aspect, the maximum drive voltage optimization device has a voltage value repetitive setting device for newly setting, when a second estimated maximum MI value calculated by using the second maximum drive voltage value exceeds the target MI value, the second maximum drive voltage value to the first maximum drive voltage value, and newly setting a value of the half of the second maximum drive voltage value to the second maximum drive voltage value.

In the eighth aspect, the voltage value repetitive setting device makes the second maximum drive voltage value to be close to an optimum value.

In a ninth aspect, in the ultrasonic imaging apparatus according to the eighth aspect, when a second estimated maximum MI value calculated by using the second maximum drive voltage value is equal to or less than the target MI value, the voltage value repetitive setting device newly sets an average value of the first and second maximum drive voltage values to the first maximum drive voltage value.

In the ninth aspect, the voltage value repetitive setting device sets the second maximum drive voltage value close to an optimum value.

In a tenth aspect, in the ultrasonic imaging apparatus according to the ninth aspect, when a second estimated maximum MI value calculated by using the second maximum drive voltage value is equal to or less than the target MI value and the difference between the target MI value and the second estimated maximum MI value does not exceed a target MI threshold, the maximum drive voltage optimization device sets the second maximum drive voltage value as an optimized maximum drive voltage value.

In the tenth aspect, a value at which the difference between the target MI value and the second estimated maximum MI value does not exceed the target MI threshold is set as an optimum value.

In an eleventh aspect, in the ultrasonic imaging apparatus according to the tenth aspect, the input unit includes a target MI threshold setting device for inputting the target MI threshold.

In the eleventh aspect, precision of optimization is adjusted.

In a twelfth aspect, in the ultrasonic imaging apparatus according to any one of the second to eleventh aspects, at the time of obtaining the tomographic image information by using a plurality of imaging modes having different scan parameter value information, the maximum drive voltage optimization device optimizes the maximum drive voltage value in each of the imaging modes.

In the twelfth aspect, the maximum drive voltage value is optimized in each of the imaging modes, so that non-destruction of the contrast agent is made more reliably.

In a thirteenth aspect, in the ultrasonic imaging apparatus according to the twelfth aspect, the input unit inputs target MI value information for each of the imaging modes.

In the thirteenth aspect, the target MI value information is optimized on the imaging mode unit basis.

In a fourteenth aspect, in the ultrasonic imaging apparatus according to the thirteenth aspect, the imaging modes include a contrast agent imaging mode and a B-mode.

In the fourteenth aspect, the imaging mode is set so as to be adapted to obtain an image of a contrast agent.

In a fifteenth aspect, in the ultrasonic imaging apparatus according to the fourteenth aspect, the input unit inputs, as a target MI value in the B-mode, a safety factor of a value equal to or less than 1 and exceeding 0, with which a target MI value in the contrast agent imaging mode is multiplied.

In the fifteenth aspect, at the time of performing imaging in the B-mode, non-destruction of a contrast agent is made reliably.

In a sixteenth aspect, in the ultrasonic imaging apparatus according to the fourteenth aspect, the input unit inputs, as a target MI value in the B-mode, a predetermined value to be subtracted from a target MI value in the contrast agent imaging mode.

In the sixteenth aspect, at the time of performing imaging in the B-mode, non-destruction of a contrast agent is made reliably.

In a seventeenth aspect, in the ultrasonic imaging apparatus according to the twelfth aspect, the maximum drive voltage optimization device has a target MI value calculating device for automatically calculating a target MI value for each of the imaging modes on the basis of the target MI value.

In the seventeenth aspect, the target MI value by mode is automatically calculated.

In an eighteenth aspect, in the ultrasonic imaging apparatus according to the seventeenth aspect, the imaging modes include a contrast agent imaging mode and a B-mode.

In the eighteenth aspect, the imaging mode is set so as to be adapted to obtain an image of a contrast agent.

In a nineteenth aspect, in the ultrasonic imaging apparatus according to the eighteenth aspect, when the target MI value is for the contrast agent imaging mode, the target MI value calculating device calculates a target MI value in the B-mode by multiplying the target MI value with a safety factor of a value equal to or less than 1 and exceeding 0.

In a twentieth aspect, in the ultrasonic imaging apparatus according to the eighteenth aspect, when the target MI value is for the contrast agent imaging mode, the target MI value calculating device calculates a target MI value in the B-mode by subtracting a predetermined value from the target MI value.

When scan parameter value information is changed in an examination using a contrast agent, a work for manually re-setting the maximum drive voltage of a piezoelectric transducer is eliminated, thereby improving operability. In addition, also in the case where the examination includes a plurality of imaging modes, the maximum drive voltage is optimized on the imaging mode unit basis, so that non-destruction of the contrast agent can be made more reliably.

Further objects and advantages of the present invention will be apparent from the following description of the preferred embodiments of the invention as illustrated in the accompanying drawings.

DETAILED DESCRIPTION OF THE INVENTION

Embodiments of an ultrasonic imaging apparatus will be described below with reference to the appended drawings. However, the invention is not limited to the embodiments described herein.

Figure 1:
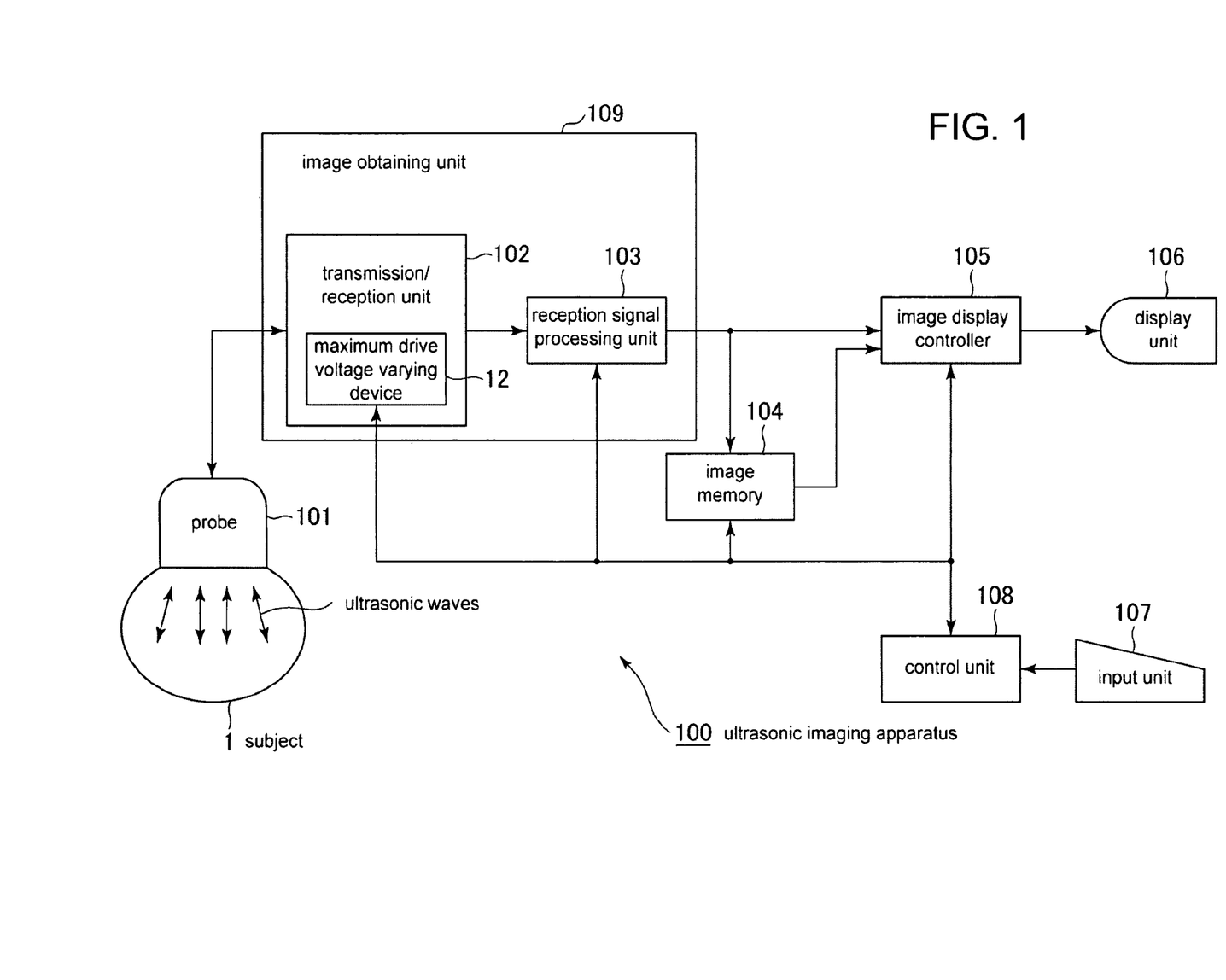
FIG. 1 is a block diagram showing a general configuration of an ultrasonic imaging apparatus.

First, a general configuration of an ultrasonic imaging apparatus 100 of the embodiment will be described. FIG. 1 is a block diagram showing a general configuration of the ultrasonic imaging apparatus 100 of the embodiment. The ultrasonic imaging apparatus 100 includes a probe 101, an image obtaining unit 109, a cine memory 104, an image display controller 105, a display unit 106, an input unit 107, and a control unit 108. The image obtaining unit 109 further includes a transmission/reception unit 102 and a reception signal processing unit 103.

The probe 101 repeatedly emits ultrasonic waves to a part for transmitting/receiving the ultrasonic waves, that is, in a specific direction of a tomographic section in a subject 1 and receives an ultrasonic signal reflected from the inside of the subject 1 as time-sequential sound rays. The probe 101 performs an electronic scan while sequentially switching the ultrasonic wave irradiation direction. In the probe 101, not-shown piezoelectric transducers are arranged in an array.

The transmission/reception unit 102 is connected to the probe 101 via a coaxial cable and performs initial amplification on an electric signal for driving the piezoelectric transducers in the probe 101 and an ultrasonic signal received. The transmission/reception unit 102 includes a maximum drive voltage varying device 12. The maximum drive voltage varying device 12 changes the maximum drive voltage for driving the piezoelectric transducers in accordance with a control signal from the control unit 108. Therefore, the maximum drive voltage varying device 12 changes the maximum sound pressure of the ultrasonic wave emitted to the subject. The control unit 108 determines the maximum drive voltage on the basis of the value of a power level PL set from the input unit 107.

The reception signal processing unit 103 generates an electric signal for driving the transmission/reception unit 102 and generates tomographic image information such as B-mode image information from an ultrasonic signal amplified by the transmission/reception unit 102. Particularly, in the case of injecting a contrast agent to the subject 1, a contrast agent mode process in which a scan parameter value is optimized to imaging with a contrast agent is performed to obtain contrast agent mode image information.

In the case of transmitting ultrasonic waves, the reception signal processing unit 103 delays a transmission signal so that focus is adjusted to a focal position. In the case of receiving ultrasonic waves, the reception signal processing unit 103 performs a process of delaying and adding a received ultrasonic signal, an A/D (analog/digital) converting process, a process of writing the converted digital information as tomographic image information into the cine memory 104 which will be described later, and the like.

The cine memory 104 stores tomographic image information and the like generated in the contrast imaging mode process. Particularly, the cine memory 104 stores the tomographic image information which changes with time together with information of time at which the information is obtained using a frame indicative of a single piece of tomographic image information of the imaging region as the minimum unit.

The image display controller 105 performs conversion of a display frame rate of the tomographic image information or the like generated by the reception signal processing unit 103, colour display control, and controls on the shapes and positions of a display image of the tomographic image information. The image display controller 105 displays an ROI (Region Of Interest) and the like on a display image of the tomographic image information and the like.

The display unit 106 visibly displays image information output from the image display controller 105 to the operator by using a CRT (Cathode Ray Tube), an LCD (Liquid Crystal Display), or the like. The display unit 106 can display a color image in accordance with an instruction from the image display controller 105.

The control unit 108 controls operations of the parts in the ultrasonic imaging apparatus 100 on the basis of an operation input signal from the input unit 107, a prestored program, and data, and displays a B-mode image or the like as the tomographic image information on the display unit 106. The control unit 108 will be described in detail later.

The input unit 107 is made by a keyboard, a pointing device, and the like. An operation input signal for selecting an imaging mode, a scan parameter value used at the time of obtaining an image, and the like are input by the operator and transmitted to the control unit 108.

Figure 2:
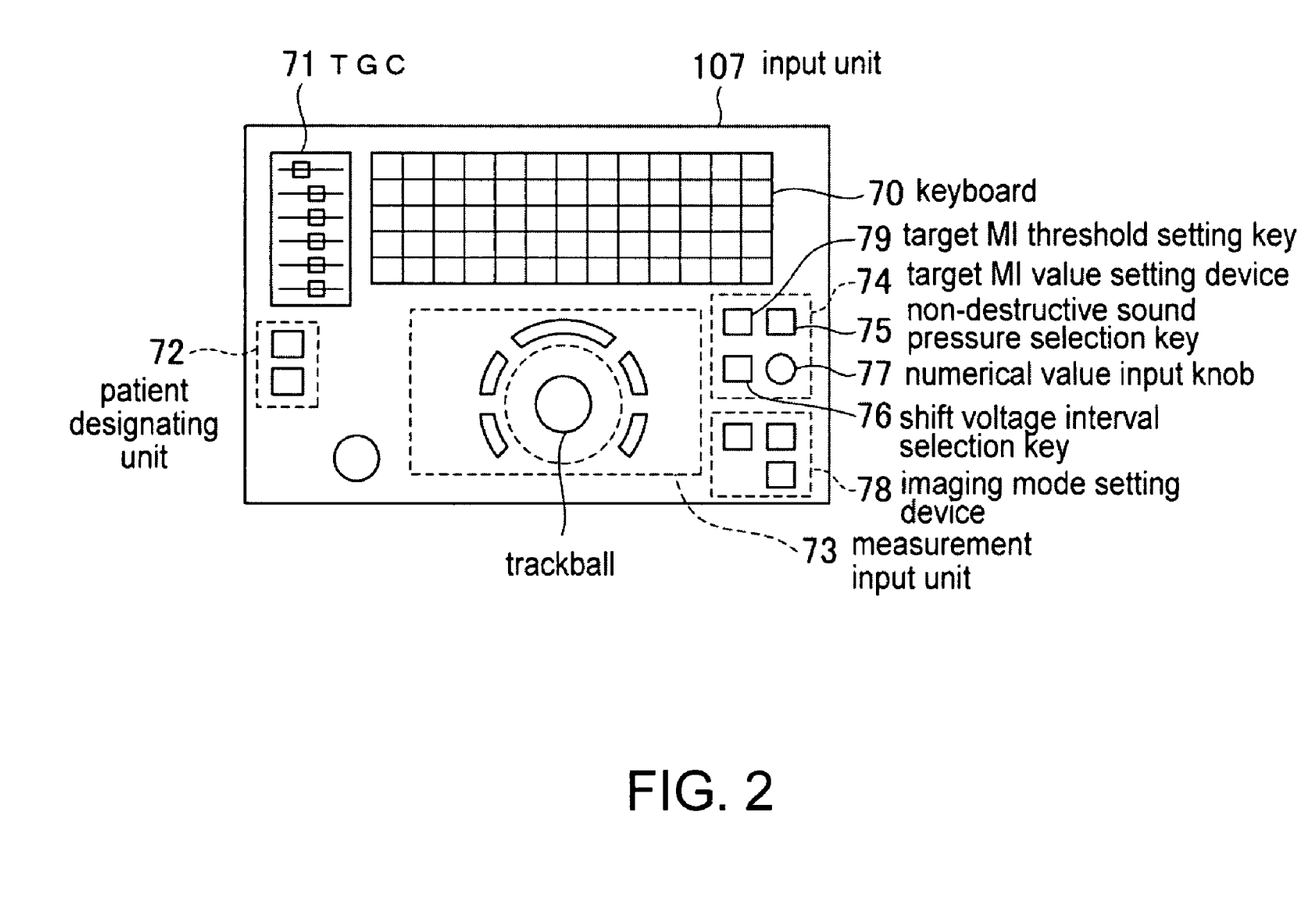
FIG. 2 is an appearance view showing the appearance of an input unit in the embodiment.

FIG. 2 is a view illustrating an example of the input unit 107. The input unit 107 includes a keyboard 70, a TGC (Time Gain Controller) 71, a patient designating unit 72 including a new patient key, a measurement input unit 73 including a track ball and also a sewing as ROI (Region Of Interest) setting device, an imaging mode setting device 78, and a target MI value setting device 74.

The TGC 71 adjusts the gain in the depth direction of tomographic image information displayed. The patient designating unit 72 includes a key selected in the case of obtaining an image of a new subject. The measurement input unit 73 has keys for setting the shape, position, size, and the like of a region of interest at the time of setting a region of interest in the display unit 106, and the function of measuring a pixel value and the like in the set region of interest. The target MI value setting device 74 inputs non-destructive sound pressure information as the upper limit value of sound pressure at which the contrast agent is not destroyed in the case of performing imaging using the contrast agent.

The target MI value setting device 74 is constructed by a nondestructive sound pressure selection key 75, a shift voltage interval selection key 76, a target MI threshold setting key 79, and a numerical value input knob 77. In the case where the non-destructive sound pressure selection key 75 is turned on, numerical value information input from the numerical value input knob 77 indicates the upper limit value of the non-destructive sound pressure of the contrast agent using MI. In the case where the shift voltage interval selection key 76 is turned on, numerical value information input from the numerical value input knob 77 indicates the value of a variation width ΔV of the maximum drive voltage used in a voltage monotonous decreasing device of a maximum drive voltage optimization which will be described later. In the case where the target MI threshold setting key 79 is turned on, numerical value information input from the numerical value input knob 77 becomes a target MI threshold δ for determining the magnitude of the difference between a target MI value which will be described later and an estimated maximum MI value.

The imaging mode setting device 78 is used to select an imaging mode such as a contrast agent imaging mode or a B-mode. Keys corresponding to the imaging modes exist, and the imaging mode corresponding to a depressed key is executed. Synchronously with the selection of the key, a key input in the target MI value setting device 74 also corresponds to the selected imaging mode.

Figure 3:
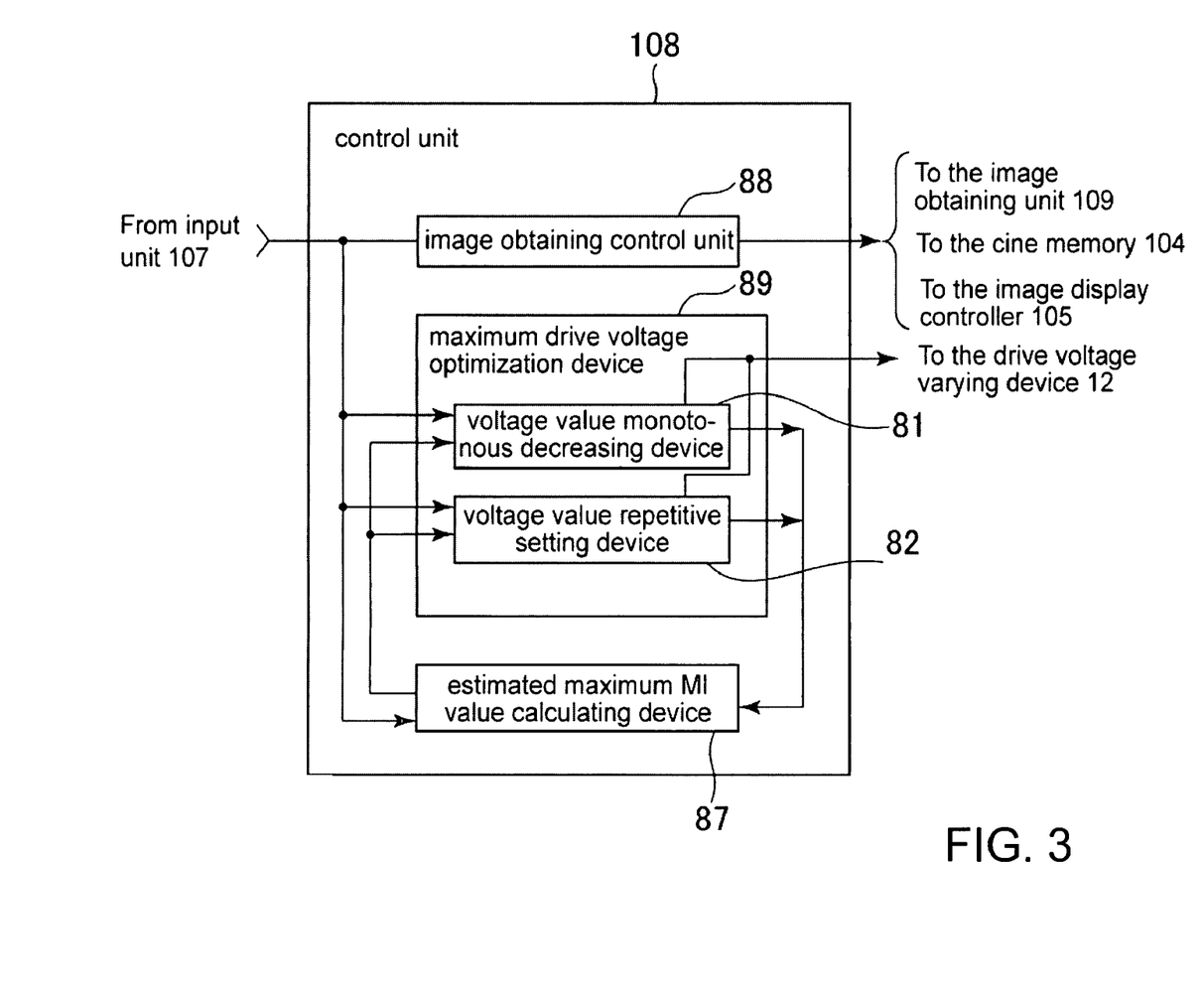
FIG. 3 is a block diagram showing the configuration of a control unit in the embodiment.

FIG. 3 is a block diagram showing the configuration of the control unit 108. The control unit 108 includes an image obtaining control unit 88, a maximum drive voltage optimization device 89, and an estimated maximum MI value calculating device 87.

The image obtaining control unit 88 performs an ultrasonic scan on the basis of scan parameter value information such as imaging mode designation information, maximum drive voltage information, focal position information, and drive frequency information, and obtains tomographic image information.

The estimated maximum MI value calculating device 87 calculates an estimated maximum MI value PMI in the subject 1 on the basis of the scan parameter value information and the maximum drive voltage information. A method of calculating the estimated maximum MI value will be described. MI expresses an index indicative of sound pressure in the subject 1. A negative sound pressure Pr3 (Mpa: mega-pascal) in a tissue in the subject 1 has the following relation.

$$MI = Pr3/f^{1/2}$$ Eq.(1)

where f (MHz: mega-hertz) denotes the center frequency of the ultrasonic wave. From the relation, the value of MI is calculated by using the value of Pr3.

The negative sound pressure Pr3 in thee tissue has the following relation using the negative sound pressure Pr under water and a conversion factor k.

$$Pr3 = k \times Pr$$ Eq.(2)

From the relation, the value of Pr3 is calculated using the value of the negative sound pressure Pr under water.

The negative sound pressure Pr under water has the following relation to a sound pressure amplitude Pm of the sound pressure that varies sinusoidally under water.

$$Pr = Pm - Ps$$ Eq.(3)

where Ps denotes static pressure (normal one atmospheric pressure). On the basis of the relation, the value of the negative sound pressure Ps under water is calculated by using the sound pressure amplitude Pm under water.

The sound pressure amplitude Pm under water is obtained from the scan parameter value and the sound pressure distribution under water experimentally calculated. The distribution of the sound pressure amplitude Pm under water based on a predetermined scan parameter value is experimentally calculated by, for example, moving a hydrophone mounted under water or the like. The distribution information of the sound pressure amplitude Pm is pre-set in the estimated maximum MI value calculating device 87 as nonvolatile information manually input from the input unit 107 or written in a ROM or the like.

Figure 4:
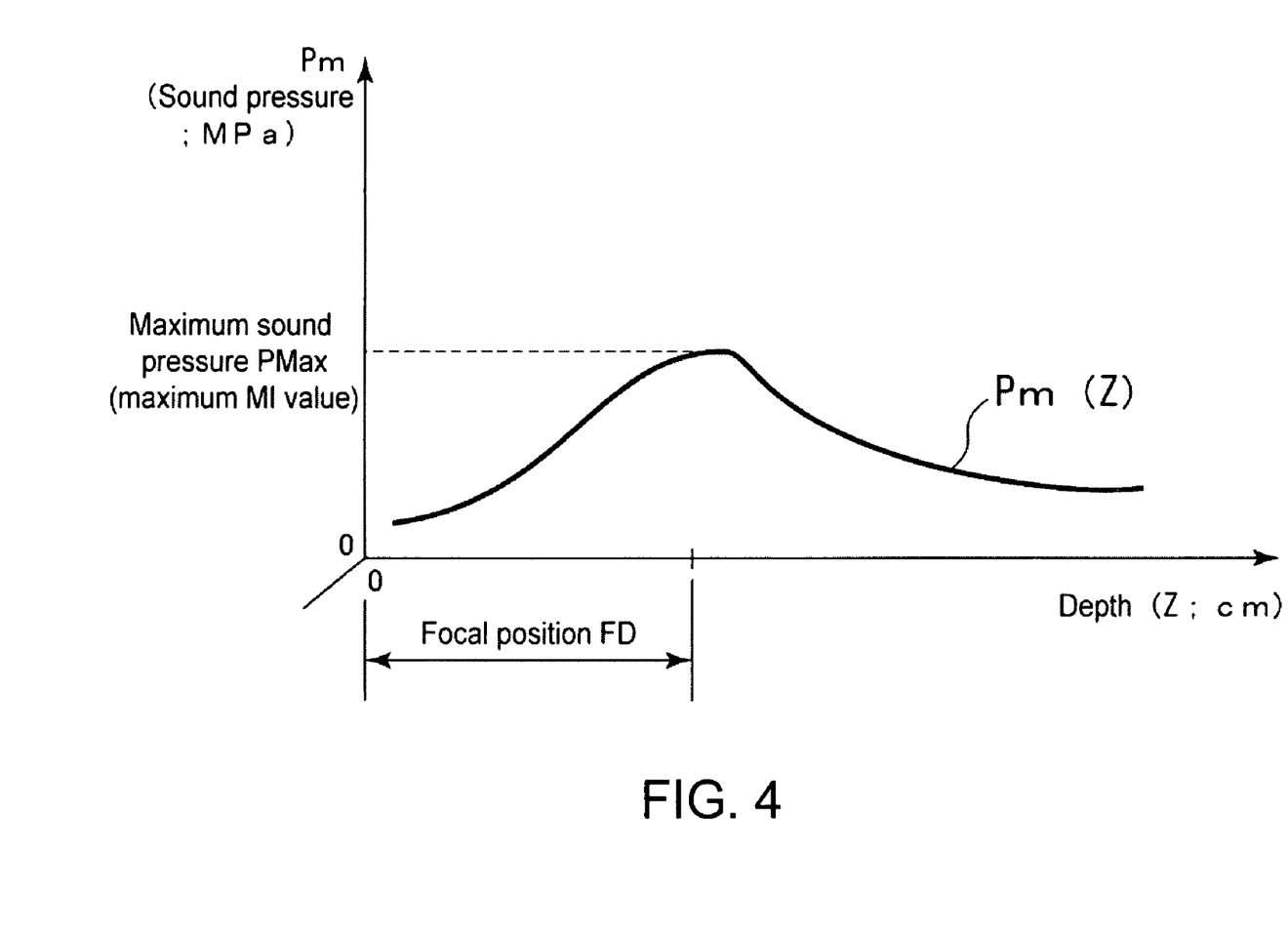
FIG. 4 is an explanatory diagram showing an example of a sound pressure distribution in the depth direction.

FIG. 4 is an explanatory diagram showing an example of a sound pressure distribution function obtained. The depth direction from the probe 101 to the inside of the subject 1 is set in the horizontal axis (z axis), and the sound pressure amplitude Pm of an ultrasonic wave emitted is set in the vertical axis. The origin of the z-axis as the horizontal axis is the surface of the probe 101 that comes into contact with the subject 1. The sound pressure distribution in the depth direction shows maximum sound pressure Pmax around the focal position FD and, after that, the sound pressure decreases gradually. The estimated maximum MI value calculating device 87 calculates the estimated maximum MI value PMI by using the above-described conversion formula using the maximum sound pressure PMax. The distribution function in the case of using the sound pressure parameter such as MI, Pr3, Pr, or the like is the same as that in the case of using the sound pressure amplitude Pm.

The sound pressure distribution information Pm(Z) as shown in FIG. 4 varies with changes in the scan parameter value. Examples of the scan parameter value which changes the sound pressure distribution are probe information Ty including resonance frequency, focal position FD of an electronic focus achieved in the scan direction, aperture width AW indicative of the number of piezoelectric transducers simultaneously driven in the scan direction, apodization information AP, and maximum drive voltage MV for driving the piezoelectric transducers. With the scan parameter values, the sound pressure distribution information Pm(Z) experimentally obtained and the maximum MI value are corrected to proper ones. The estimated maximum MI value PMI can be expressed as follows when the correction factor is indicated as "f".

$$PMI = f(MV, Ty, FD, AW, AP, \ldots)$$ Eq. (4)

The correction factor "f" has a complicated function form. It is easy to obtain PMI on the left side from the operation part on the right side. However, it is not easy to determine one variable in the right-side operation part, for example, the maximum drive voltage MV by using PMI as an independent variation.

Referring again to FIG. 3, the maximum drive voltage optimization device 89 optimizes the maximum drive voltage MV by using the correction factor "f". In the optimization, the maximum drive voltage MV when the estimated maximum MI value PMI becomes the maximum at the target MI value or less is obtained. At the maximum drive voltage MV, the sound pressure in the subject 1 does not exceed the target MI value, destruction of the contrast agent is prevented, and tomographic image information of the maximum sensitivity is obtained under this condition.

The maximum drive voltage optimization device 89 includes a voltage value monotonous decreasing device 81 and a voltage value repetitive setting device 82. The voltage value monotonous decreasing device 81 and the voltage value repetitive setting device 82 include two different methods of optimizing the maximum drive voltage DV. Any one of the methods is selected and executed. The functions and operations of the voltage value monotonous decrease device 81 and the voltage value repetitive setting device 82 will be described in detail in the following explanation of the operation of the control unit 108.

Figure 5:
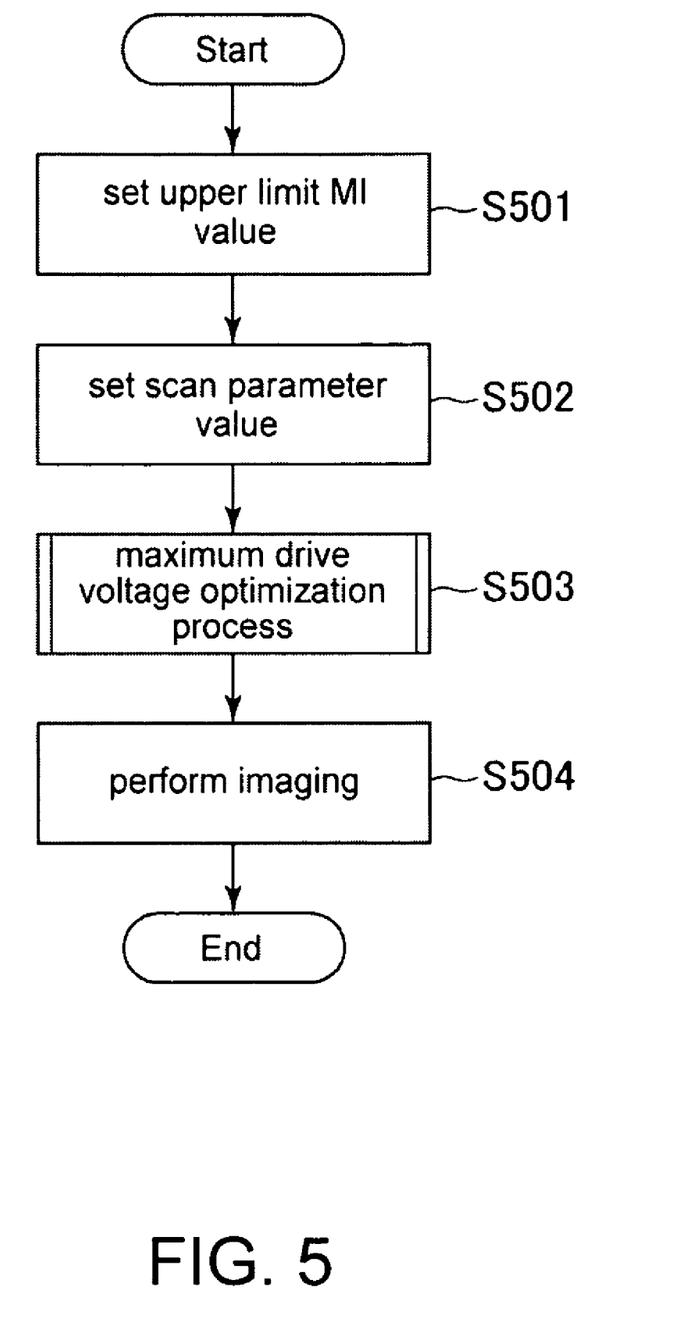
FIG. 5 is a flowchart showing operations of the control unit in the embodiment.

The operation of the control unit 108 in the embodiment will now be described. FIG. 5 is a flowchart showing the operation of the control unit 108. First, the operator enters the target MI value indicative of the upper limit of the non-destructive sound pressure of the contrast agent by using the target MI value setting device 74 in the input unit 107 (step S501). In the case of optimizing the maximum drive voltage by using the voltage value monotonous decreasing device 81, the operator simultaneously selects the shift voltage interval selecting key 76 to enter the shift voltage interval ΔV as a variation width at the time of varying the maximum drive voltage.

After that, the operator sets the scan parameter values for imaging (step S502). The operator sets focal position, aperture width, and the like optimum to draw the contrast agent.

Figure 6:
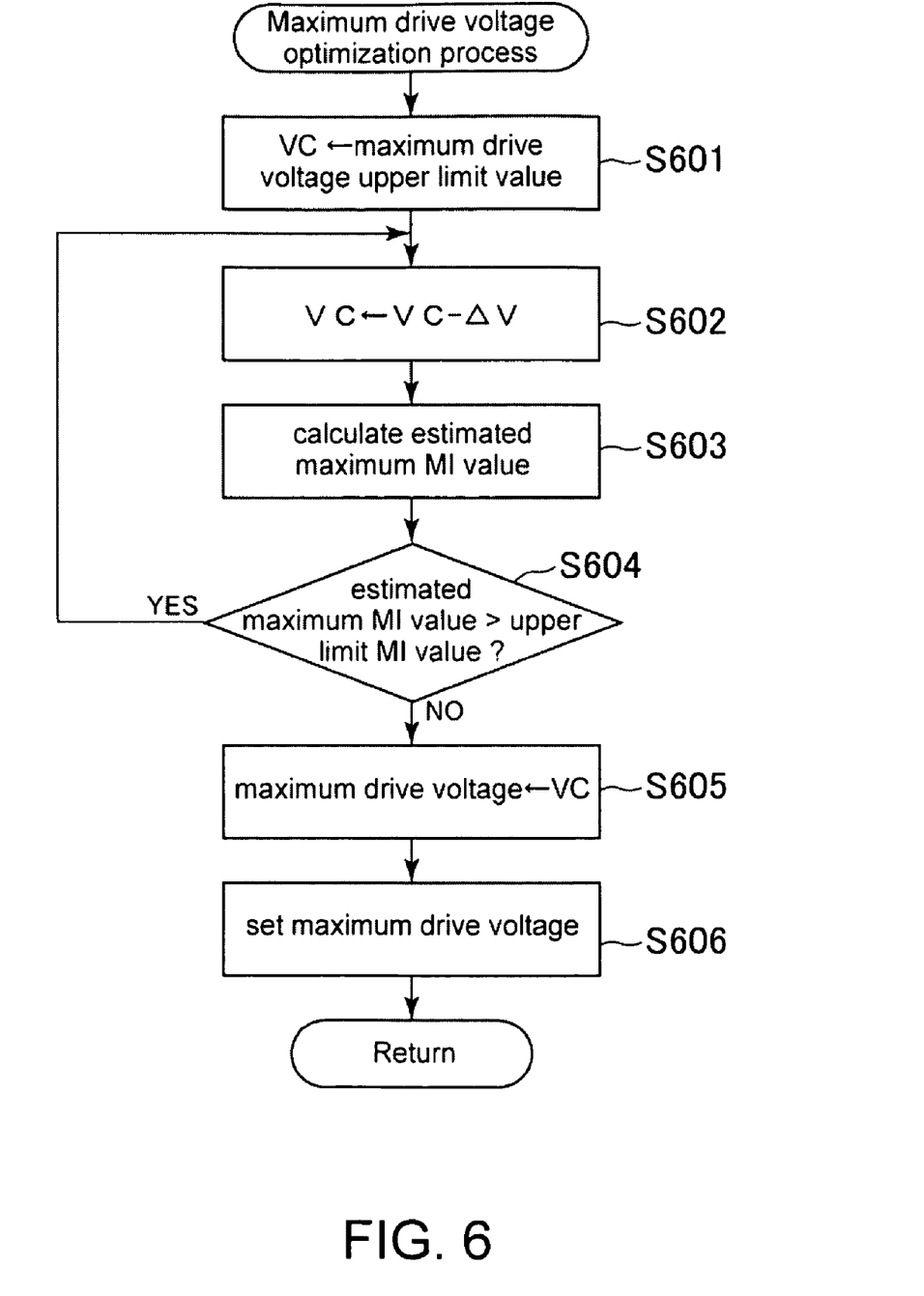
FIG. 6 is a flowchart showing operations of maximum drive voltage optimization process using a voltage value monotonous decreasing device.

After that, the maximum drive voltage optimization device 89 performs maximum drive voltage optimization process using the target MI value and the scan parameter values that are set (step S503). FIG. 6 is a flowchart showing the maximum drive voltage optimization process in the case of using the voltage value monotonous decreasing device 81. First, the voltage value monotonous decreasing device 81 sets the maximum drive voltage upper limit value which can be set in the maximum drive voltage varying device 12 for VC as a voltage variable indicative of the maximum drive voltage (step S601).

The voltage value monotonous decreasing device 81 sets, as a new voltage variable VC, a value obtained by subtracting the shift voltage interval ΔV entered by using the target MI value setting device 74 from VC as a voltage variable (step S602). The voltage interval of about 1% to a few % of the maximum drive voltage upper limit value is set, and the shift voltage interval ΔV entered by using the target MI value setting device 74 is determined in consideration of precision of optimization and computation time.

The maximum drive voltage optimization device 89 transmits the information of the value of the voltage variable VC to the estimated maximum MI value calculating device 87, and calculates the estimated maximum MI value PMI (step S603). The maximum drive voltage optimization device 89 transmits information of the calculated estimated maximum MI value from the estimated maximum MI value calculating device 87 to the voltage value monotonous decreasing device 81.

After that, the voltage value monotonous decreasing device 81 determines whether the calculated estimated maximum MI value is larger than the target MI value or not (step S604). When the estimated maximum MI value is larger than the target MI value (YES in step S604), due to the possibility that the contrast agent is destroyed, the voltage value monotonous decreasing device 81 shifts to step S602 and decreases the value of the voltage variable VC only by the shift voltage interval ΔV, and the steps S603 and S604 are repeated.

In the case where the estimated maximum MI value is equal to or less than the target MI value (NO in step S604), the contrast agent is not destroyed, so that the voltage value monotonous decreasing device 81 sets the value of the voltage variable VC as the value of the maximum drive voltage (step S605). The voltage value monotonous decreasing device 81 sets the value of the maximum drive voltage as the maximum drive voltage of the maximum drive voltage varying device 12 (step S606).

When the estimated maximum MI value is set to the target MI value or less and the voltage variable VC is changed in the shift voltage interval ΔV, the value of the maximum drive voltage is used to set the maximum estimated maximum MI value at the target MI value or less.

Figure 7:
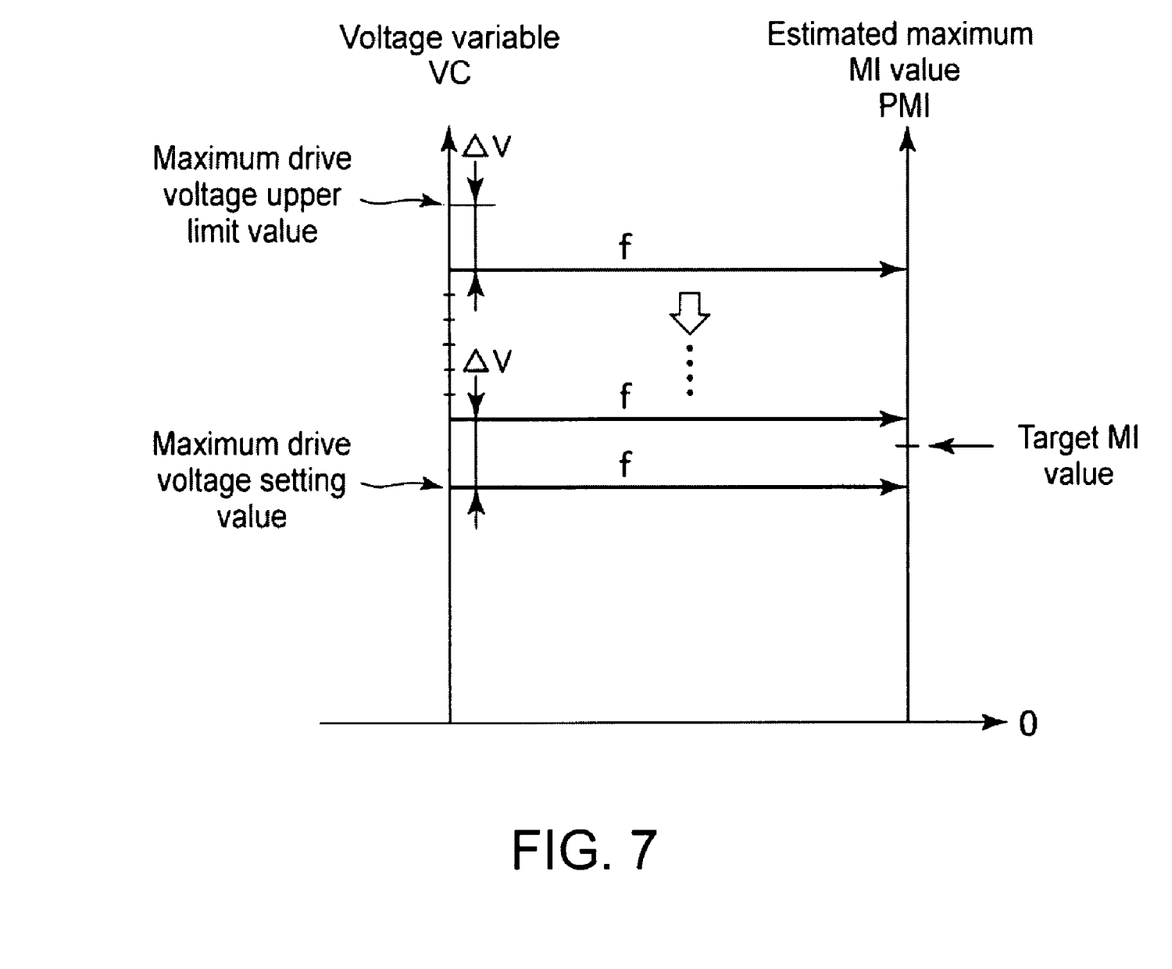
FIG. 7 is an explanatory diagram schematically showing operations of the voltage value monotonous decreasing device.

FIG. 7 is a schematic diagram schematically showing processes for setting the maximum drive voltage. The vertical axis on the left side indicates the value of the voltage variable VC, and the vertical axis on the right side indicates the estimated maximum MI value PMI obtained by using the function "f". In the axes, the higher, the larger the value is. The function "f" is a monotonous increase function with which the estimated maximum MI value also increases as the voltage variable VC increases. Initially, using a value close to the maximum drive voltage upper limit value as the voltage variable VC, the estimated maximum MI value is calculated. After that, the value of the voltage value VC is gradually decreased, and the value of the maximum drive voltage at which the estimated maximum MI value becomes the initial MI value or less is used as a set value of the maximum drive voltage varying device 12.

Figure 8:
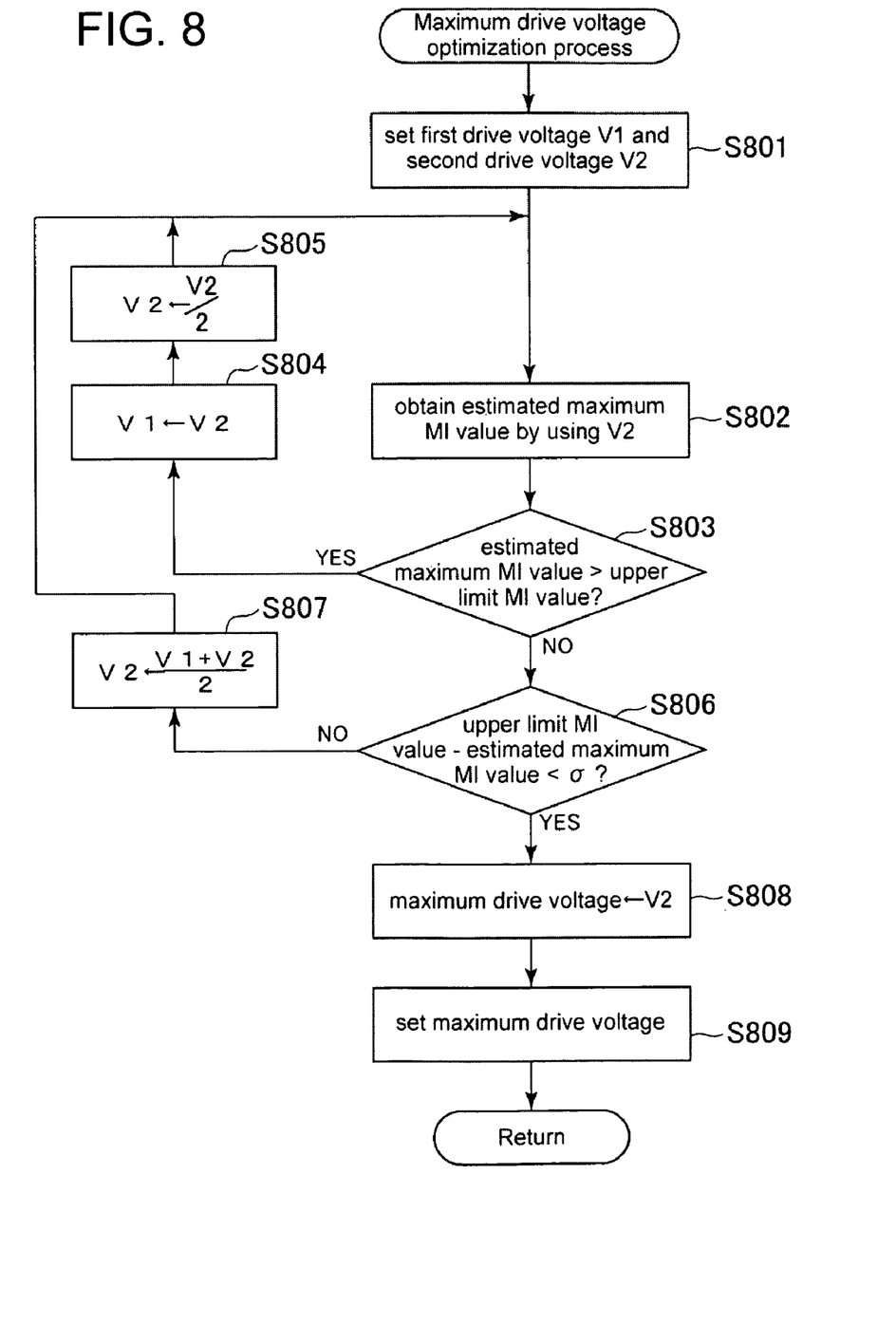
FIG. 8 is a flowchart showing operations of the maximum drive voltage optimization process using a voltage value repetitive setting device.

In the maximum drive voltage optimization process in the step S503, the example using the voltage value monotonous decreasing device 81 has been described. Alternately, the maximum drive voltage optimization process can be also performed by using the voltage value repetitive setting device 82. FIG. 8 is a flowchart showing the maximum drive voltage optimization process in the case of using the voltage value repetitive setting device 82.

First, the voltage value repetitive setting device 82 sets, as initial values, a first maximum drive voltage V1 and a second maximum drive voltage V2 smaller than the first maximum drive voltage V1 (step S801). The first maximum drive voltage V1 is, for example, the maximum drive voltage upper limit value of the maximum drive voltage varying device 12. The second maximum drive voltage V2 is set to a value that is the half of the maximum drive voltage upper limit value. The maximum drive voltage optimization device 89 transmits the second maximum drive voltage V2 to the estimated maximum MI value calculating device 87.

After that, the estimated maximum MI value calculating device 87 calculates the estimated maximum MI value PMI by using the second maximum drive voltage V2 (step S802). The estimated maximum MI value is sent back to the voltage value repetitive setting device 82. The voltage value repetitive setting device 82 determines whether the estimated maximum MI value is larger than the target MI value or not (step S803). When the estimated maximum MI value is larger than the target MI value (YES in step S803), the voltage value repetitive setting device 82 newly sets the value of the second maximum drive voltage V2 as a value of the first maximum drive voltage V1 (step S 804), newly sets the value of the half of the second maximum drive voltage V2 as a value of the second maximum drive voltage V2 (step S805), and shifts to the step S802.

Figure 9A:
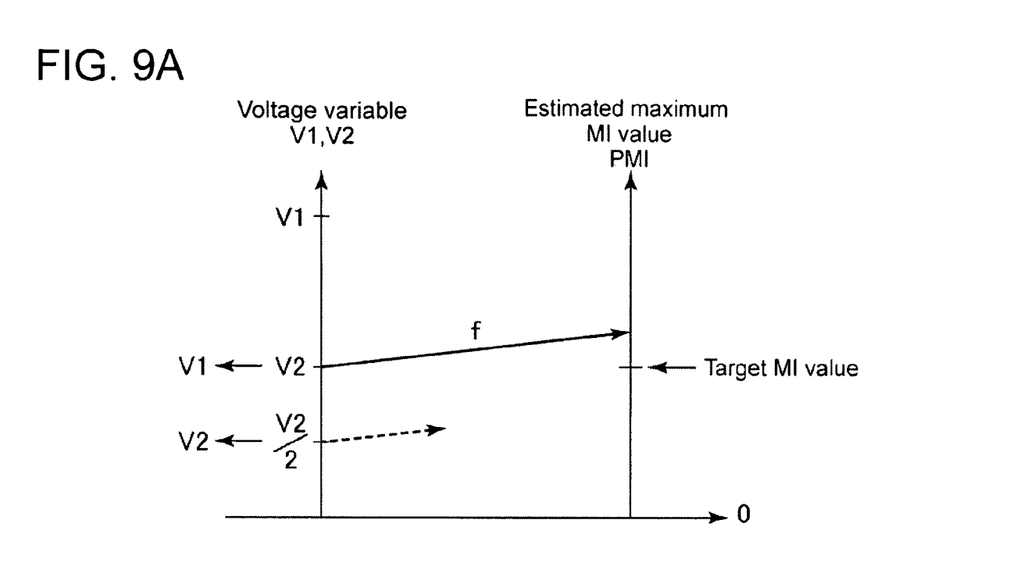
FIGS. 9A and 9B are explanatory diagrams schematically showing operations of the voltage value repetitive setting device.

FIG. 9A is a schematic diagram similar to FIG. 7, schematically showing the processes in the steps S803 to S805. The vertical axis on the left side of FIG. 9A indicates the values of the voltage variables V1 and V2, and the vertical axis on the right side indicates the estimated maximum MI value. One estimated maximum MI value is calculated by using the function "f" for one value of the voltage variable. FIG. 9A shows the processes performed in the case of YES in step S 803. In the case where the estimated maximum MI value of the voltage variable V2 exceeds the target MI value, the second maximum drive voltage V2 is newly set as the first maximum drive voltage V1, and the value of the half of the second maximum drive voltage V2 is newly set as the second maximum drive voltage V2.

Referring again to FIG. 8, in the case where the estimated maximum MI value is equal to or less than the target MI value (NO in step S803), the voltage value repetitive setting device 82 determines whether the error obtained by subtracting the estimated maximum MI value from the target MI value is within the set target MI threshold δ or not (step S806). In this case, the target MI threshold δ is a preset empirical value. The smaller the target MI threshold δ is, the more the estimated maximum MI value becomes close to the target MI value. The sensitivity of tomographic image information obtained can be increased. On the other hand, computation time necessary to optimize the second maximum drive voltage V2 becomes longer.

When the error obtained by subtracting the estimated maximum MI value from the target MI value is out of the target MI threshold δ (NO in step S806), the voltage value repetitive setting device 82 newly sets an average value of the first and second maximum drive voltages V1 and V2 as the value of the second maximum drive voltage V2 (step S807), and shifts to step S802.

Figure 9B:
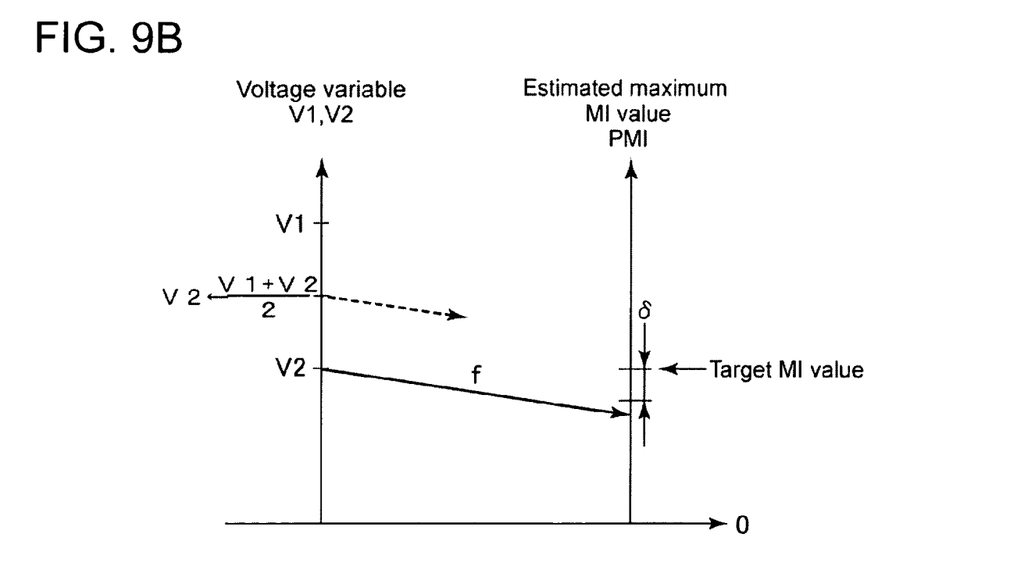

FIG. 9B is a schematic diagram similar to FIG. 9A, schematically showing the processes in the steps S803, S806, and S807. The vertical axis on the left side of FIG. 9B indicates the values of the voltage variables V1 and V2, and the vertical axis on the right side indicates the estimated maximum MI value. One estimated maximum MI value is calculated by using the function "f" for one value of the voltage variable. FIG. 9B shows the processes performed in the case of NO in steps S803 and S806. That is, FIG. 9B shows an example in which when the estimated maximum MI value of the voltage variable V2 is equal to or less than the target MI value, whether the error obtained by subtracting the estimated maximum MI value from the target MI value lies in the target MI threshold δ or not. When the error is not included in the error range of the target MI threshold δ, an average value of the first and second maximum drive voltages V1 and V2 is newly set as the second maximum drive voltage V2.

Referring again to FIG. 8, in the case where the error obtained by subtracting the estimated maximum MI value from the target MI value is within the target MI threshold δ (YES in step S806), the voltage value repetitive setting device 82 sets the value of the second maximum drive voltage V2 as a maximum drive voltage to be obtained (step S808). The value is set as the maximum drive voltage in the maximum drive voltage varying device 12 (step S809), and the maximum drive voltage optimization process is finished.

After that, referring again to FIG. 5, the operator injects the contrast agent to the subject 1, performs imaging (step S504), and finishes the process.

As described above, in the embodiment, the maximum drive voltage at which the estimated maximum MI value becomes the maximum value which does not exceed the set target MI value is obtained by the maximum drive voltage optimization device 89, and the maximum drive voltage is set in the maximum drive voltage varying device 12. Consequently, also in the case where the scan parameter values are changed, the operator can perform a reliable contrast agent examination that does not destroy the contrast agent without an effort of resetting the maximum drive voltage.

In the embodiment, the maximum drive voltage optimization device 89 performs the maximum drive voltage optimization process in the specific imaging mode that is set by the operator. The maximum drive voltage optimization device 89 can perform the process also in the case where a plurality of imaging modes are set mixedly. However, since there is a case that the scam parameter values vary among the imaging modes, the optimization is performed in each of the imaging modes. For example, a scan using a phase inversion method of obtaining an image of the contrast agent and a scan using the B-mode of obtaining background image information of the contrast agent are performed alternatively. In the case of obtaining information of one tomographic image, the scan parameter values of each of the imaging modes are used, and the maximum drive voltage is optimized on the imaging mode unit basis.

In the case where the plurality of imaging modes exist, the target MI values to be set may vary among the imaging modes. For example, in imaging in the B-mode performed to obtain a background image, to reliably prevent destruction of the contrast agent, a target MI value smaller than the target MI value which is set in the imaging mode such as the phase inversion method can be also set.

In this case, the target MI value setting device 74 inputs the target MI value in the imaging mode selected by the imaging mode setting device 78 from the numerical value input knob 77. The numerical value information input from the numerical value input knob 77 can be set as a safety factor value "k" having a value satisfying the relation $0 < k \leq 1.0$, with which the target MI value set in the contrast agent imaging mode is multiplied, or a predetermined MI value to be subtracted from the target MI value set in the contrast agent imaging mode.

In the case where the plurality of imaging modes mixedly exist, a target MI value for each of the imaging modes can be also automatically calculated and set. In this case, the maximum drive voltage optimization device 89 has a target MI value calculating device, and the target MI value calculating device automatically calculates the target MI value by imaging mode from the preset target MI value. In the case where the imaging mode includes the contrast agent imaging mode and the B-mode and the preset target MI value is for the contrast agent imaging mode, the target MI value calculating device sets a value obtained by multiplying the target MI value with the safety factor "k" or a value obtained by subtracting the predetermined MI value from the target MI value as the target MI value of the B-mode.

Although the optimization process is performed by using MI in the embodiment, similarly, optimization can be also performed by using the sound pressure parameter as the index of the sound pressure in the subject 1 such as the negative sound pressures Pr3 and Pr or the sound pressure amplitude Pm.

Many widely different embodiments of the invention may be configured without departing from the spirit and the scope of the present invention. It should be understood that the present invention is not limited to the specific embodiments described in the specification, except as defined in the appended claims.

What is claimed is:
1. An ultrasonic imaging apparatus comprising:
    an image obtaining unit configured to irradiate an imaging region in a subject into which a contrast agent is injected with an ultrasonic wave, and to obtain tomographic image information that draws the imaging region;

an input unit configured to input scan parameter value information which is set in said image obtaining unit and a target sound pressure parameter value of a sound pressure parameter as an index of an estimated sound pressure in the subject;

an estimated maximum sound pressure parameter value calculating device configured to calculate, at the time of performing the irradiation, an estimated maximum sound pressure parameter value in the subject based on the scan parameter value information and maximum drive voltage information of a piezoelectric transducer group configured to generate the ultrasonic wave, wherein the maximum drive voltage information includes a first maximum drive voltage value at which the estimated maximum sound pressure parameter value exceeds the target sound pressure parameter value and a second maximum drive voltage value smaller than the first maximum drive voltage value; and a maximum drive voltage optimization device configured to compare, each time the scan parameter value information is changed, the estimated maximum sound pressure parameter value and the target sound pressure parameter value with each other and to optimize a maximum drive voltage value of the maximum drive voltage information, wherein said maximum drive voltage optimization device comprises a voltage value repetitive setting device configured to set, when a second estimated maximum sound pressure parameter value calculated by using the second maximum drive voltage value exceeds the target sound pressure parameter value, the second maximum drive voltage value to the first maximum drive voltage value, and to set a value of half of the second maximum drive voltage value to the second maximum drive voltage value.

2. The ultrasonic imaging apparatus according to claim 1, wherein when a second estimated maximum soound pressure parameter value calculated by using the second maximum drive voltage value is equal to or less than the target sound pressure parameter value, said voltage value repetitive setting device newly is configured to set an average value of the first and second maximum drive voltage values to the first maximum drive voltage value.

3. The ultrasonic imaging apparatus according to claim 2, wherein when a second estimated maximum sound pressure parameter value calculated by using the second maximum drive voltage value is equal to or less than the target sound pressure parameter value and a difference between the target sound pressure parameter value and the second estimated maximum sound pressure parameter value does not exceed a target sound pressure parameter threshold, said maximum drive voltage optimization device is configured to set the second maximum drive voltage value as an optimized maximum drive voltage value.

4. The ultrasonic imaging apparatus according to claim 3, wherein said input unit comprises a target sound pressure parameter threshold setting device configured to input the target sound pressure parameter threshold.

5. An ultrasonic imaging apparatus comprising:
an image obtaining unit configured to irradiate an imaging region in a subject into which a contrast agent is injected with an ultrasonic wave, and to obtain tomographic image information that draws the imaging region;
an input unit configured to input scan parameter value information which is set in said image obtaining unit and a target MI value in the subject;
an estimated maximum MI value calculating device configured to calculate, at the time of performing the irradiation, an estimated maximum MI value in the subject based on the scan parameter value information and maximum drive voltage information of a piezoelectric transducer group for configured to generate the ultrasonic wave; and
a maximum drive voltage optimization device configured to compare, each time the scan parameter value information is changed, the estimated maximum MI value and the target MI value with each other and to optimize a maximum drive voltage value of the maximum drive voltage information, wherein the maximum drive voltage optimization device includes a voltage value monotonous decreasing device configured to gradually decrease a drive voltage value of the piezoelectric transducer group from an overvoltage value at which the estimated maximum MI value exceeds the target MI value at a predetermined voltage interval.

6. The ultrasonic imaging apparatus according to claim 5, wherein said input unit comprises a voltage interval setting device configured to set the voltage interval.

7. The ultrasonic imaging apparatus according to claim 5, wherein said maximum drive voltage optimization device is configured to set an initial maximum drive voltage value at which the estimated maximum MI value becomes equal to or less than the target MI value to an optimized maximum drive voltage value.

8. The ultrasonic imaging apparatus according to claim 5, wherein at the time of obtaining the tomographic image information by using a plurality of imaging modes having different scan parameter value information, said maximum drive voltage optimization device is configured to optimize the maximum drive voltage value in each of the imaging modes.

9. The ultrasonic imaging apparatus according to claim 8, wherein said input unit is configured to input target MI value information for each of the imaging modes.

10. The ultrasonic imaging apparatus according to claim 9, wherein the imaging modes include a contrast agent imaging mode and a B-mode.

11. The ultrasonic imaging apparatus according to claim 10, wherein said input unit is configured to input, as a target MI value in the B-mode, a safety factor of a value equal to or less than 1 and exceeding 0, with which a target MI value in the contrast agent imaging mode is multiplied.

12. The ultrasonic imaging apparatus according to claim 10, wherein said input unit is configured to input, as a target MI value in the B-mode, a predetermined value to be subtracted from a target MI value in the contrast agent imaging mode.

13. The ultrasonic imaging apparatus according to claim 8, wherein said maximum drive voltage optimization device comprises a target MI value calculating device configured to automatically calculate a calculated target MI value for each of the imaging modes based on the target MI value.

14. The ultrasonic imaging apparatus according to claim 13, wherein the imaging modes include a contrast agent imaging mode and a B-mode.

15. The ultrasonic imaging apparatus according to claim 14, wherein when the target MI value is for the contrast agent imaging mode, said target MI value calculating device is configured to calculate a calculated target MI value in the B-mode by multiplying the target MI value with a safety factor of a value equal to or less than 1 and exceeding 0.

16. The ultrasonic imaging apparatus according to claim 14, wherein when the target MI value is for the contrast agent imaging mode, said target MI value calculating device is configured to calculate a calculated target MI value in the B-mode by subtracting a predetermined value from the target MI value.

* * * * *